(12) United States Patent
Ghods et al.

(10) Patent No.: US 10,739,289 B2
(45) Date of Patent: *Aug. 11, 2020

(54) ELECTRICAL METHODS AND SYSTEMS FOR CONCRETE TESTING

(71) Applicant: GIATEC SCIENTIFIC INC., Ottawa OT (CA)

(72) Inventors: Pouria Ghods, Gloucester (CA); Rouhollah Alizadeh, Nepean (CA); Mustafa Salehi, Nepean (CA)

(73) Assignee: Gaitec Scientific Inc., Ottawa, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/385,304

(22) Filed: Apr. 16, 2019

(65) Prior Publication Data
US 2019/0242840 A1    Aug. 8, 2019

Related U.S. Application Data

(63) Continuation of application No. 15/496,298, filed on Apr. 25, 2017, now Pat. No. 10,571,418, which is a
(Continued)

(51) Int. Cl.
*G01R 27/08* (2006.01)
*G01N 27/04* (2006.01)
(Continued)

(52) U.S. Cl.
CPC ............. *G01N 27/04* (2013.01); *G01N 17/02* (2013.01); *G01N 17/04* (2013.01); *G01N 27/02* (2013.01);
(Continued)

(58) Field of Classification Search
CPC ...... G01N 17/00; G01N 17/006; G01N 17/02; G01N 17/04
(Continued)

(56) References Cited

U.S. PATENT DOCUMENTS

2007/0210814 A1*  9/2007  Albadri ............... G01N 27/223
                                                             73/78
2008/0042901 A1*  2/2008  Smith .................... G01S 5/021
                                                            342/464
(Continued)

*Primary Examiner* — Raul J Rios Russo
(74) *Attorney, Agent, or Firm* — Rosenberg, Klein & Lee

(57) ABSTRACT

Hundreds of thousands of concrete bridges and hundreds of billions of tons of concrete require characterization with time for corrosion. Accordingly, protocols for rapid testing and improved field characterization systems that automatically triangulate electrical resistivity and half-cell corrosion potential measurements would be beneficial allowing discrete/periodic mapping of a structure to be performed as well as addressing testing for asphalt covered concrete. Further, it is the low frequency impedance of rebar in concrete that correlates to corrosion state but these are normally time consuming vulnerable to noise. Hence, it would be beneficial to provide a means of making low frequency electrical resistivity measurements rapidly. Further, prior art techniques for electrical rebar measurements require electrical connection be made to the rebar which increases measurement complexity/disruption/repair/cost even when no corrosion is identified. Beneficially a method of determining the state of a rebar without electrical contact is taught.

21 Claims, 12 Drawing Sheets

Related U.S. Application Data continuation of application No. 14/168,254, filed on Jan. 30, 2014, now Pat. No. 9,638,652.

(60) Provisional application No. 61/758,309, filed on Jan. 30, 2013.

(51) Int. Cl.

| | |
|---|---|
| *G01N 17/02* | (2006.01) |
| *G01N 33/38* | (2006.01) |
| *G01N 27/02* | (2006.01) |
| *G01N 17/04* | (2006.01) |
| *G01L 1/10* | (2006.01) |
| *G01N 17/00* | (2006.01) |
| *G01L 1/20* | (2006.01) |
| *G01L 1/22* | (2006.01) |
| *G01R 27/00* | (2006.01) |

(52) U.S. Cl.
CPC ......... *G01N 27/026* (2013.01); *G01N 33/383* (2013.01); *G01L 1/10* (2013.01); *G01L 1/20* (2013.01); *G01L 1/22* (2013.01); *G01N 17/00* (2013.01); *G01N 17/006* (2013.01); *G01R 27/00* (2013.01)

(58) Field of Classification Search
USPC ........ 324/71.2, 76, 439, 459, 549, 600, 635, 324/639, 644, 649, 662, 671, 691, 693, 324/700, 716
See application file for complete search history.

(56) References Cited

U.S. PATENT DOCUMENTS

| | | | |
|---|---|---|---|
| 2008/0055158 A1* | 3/2008 | Smith | G01S 5/021 342/464 |
| 2010/0073235 A1* | 3/2010 | Smith | G01S 5/021 342/451 |
| 2016/0291060 A1* | 10/2016 | Wood | G01R 11/25 |
| 2018/0252748 A1* | 9/2018 | Wood | G01R 19/0092 |

* cited by examiner

210

220

230

240

250

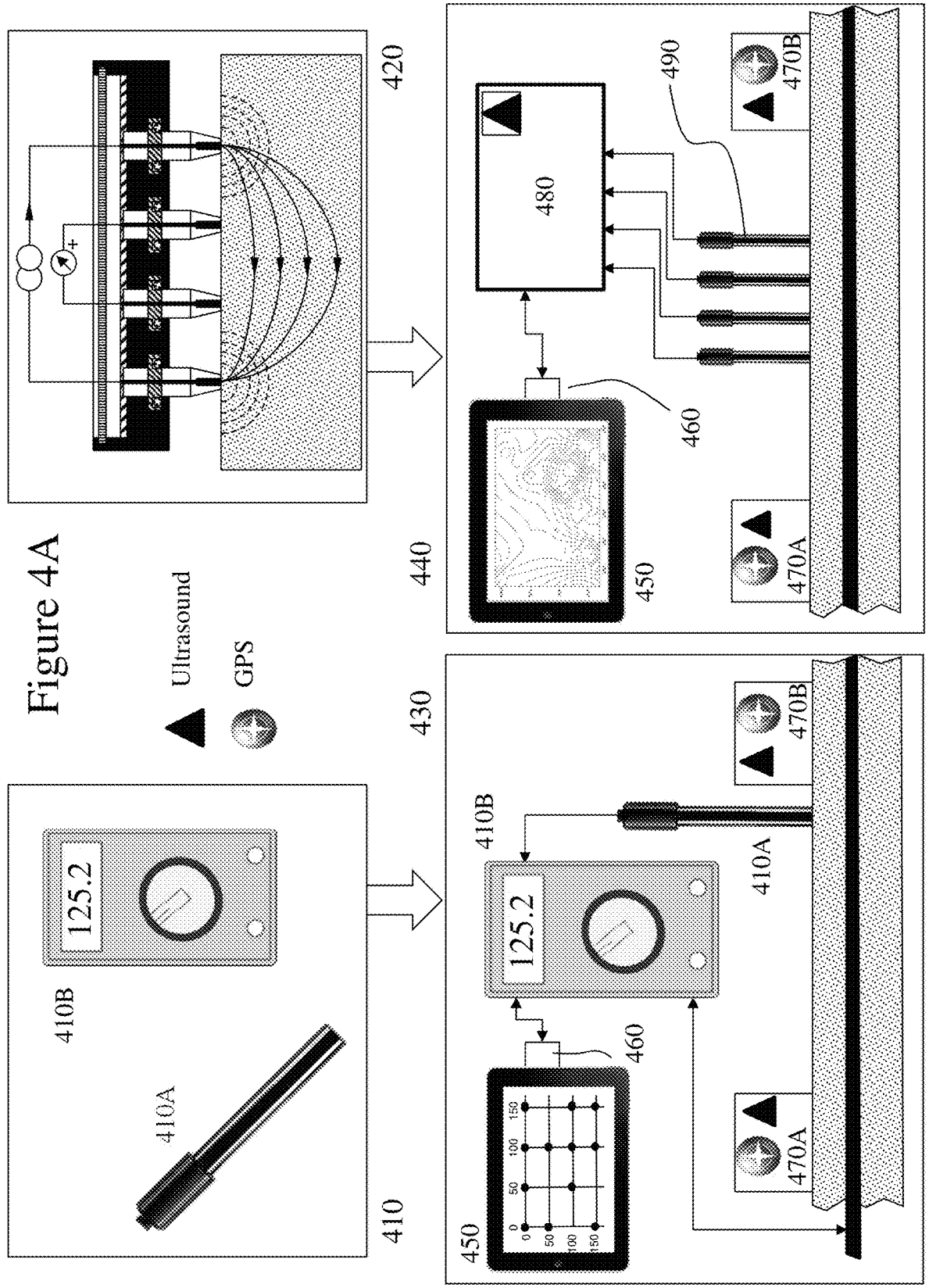

ELECTRICAL METHODS AND SYSTEMS FOR CONCRETE TESTING

CROSS-REFERENCE TO RELATED APPLICATIONS

This patent application claims the benefit as a continuation of U.S. patent application Ser. No. 15/496,298 filed Apr. 25, 2017 entitled "Electrical Methods and Systems for Concrete Testing" which itself claims the benefit of priority from U.S. patent application Ser. No. 14/168,254 filed on Jan. 30, 2014 entitled "Electrical Methods and Systems for Concrete Testing" which itself claims the benefit of priority from U.S. Provisional Patent Application 61/758,309 filed on Jan. 30, 2013 entitled "Electrical Methods and Systems for Concrete Testing."

FIELD OF THE INVENTION

The present invention relates to concrete testing and more particularly to electrical methods and systems for corrosion measurement of rebar in reinforced concrete structures.

BACKGROUND OF THE INVENTION

Concrete can be one of the most durable building materials and structures made of concrete can have a long service life. Concrete is a composite construction material composed primarily of aggregate, cement, and water. It provides superior fire resistance, compared with wooden construction and can gain strength over time. Further, as it is used as liquid that subsequently hardens it can be formed into complex geometries and may poured either directly into formworks at the construction sites (so called ready mix concrete) or employed remotely to pre-build concrete elements and structures. Overall concrete is the most widely used construction material in the world with an annual consumption estimated at approximately 30 billion tons in 2006, compared to 2 billion in 1950. During the next 5 years concrete consumption is estimated to grow with a Compound Annual Growth Rate (CAGR) between 6% and 9% according to market forecasts of cement and concrete admixtures globally over the period 2012 to 2017 such that the 30 billion ton consumption will increase to approximately 40 billion tons.

Concrete technology was known by the Ancient Romans and was widely used within the Roman Empire, the Colosseum in Rome is largely built of concrete. After the Empire passed, use of concrete became scarce until the technology was re-pioneered in the mid-18th century with developments such as the method of producing Portland cement patented by Joseph Aspdin in 1824. There are many types of concrete available, created by varying the proportions of the main ingredients of cement, aggregate, and water as well as reinforcement means, chemical admixtures, and mineral admixtures. In this way or by substitution for the cemetitious and aggregate phases, the finished product can be tailored to its application with varying strength, density, or chemical and thermal resistance properties.

Examples of chemical admixtures include accelerators to speed up the hardening of concrete, retarders to slow the hardening of concrete for large or difficult pours, air entrainments to capture air bubbles, plasticizers to increase workability, pigments for colour, corrosion inhibitors, bonding agents and pumping aids. Recently the use of recycled materials as concrete ingredients has been gaining popularity because of increasingly stringent environmental legislation. The most conspicuous of these is fly ash, a by-product of coal-fired power plants. This use reduces the amount of quarrying and landfill space required as the ash acts as a cement replacement thus reducing the amount of cement required.

Concrete is widely used for making architectural structures, foundations, brick/block walls, pavements, bridges/overpasses, motorways/roads, runways, parking structures, dams, pools/reservoirs, pipes, footings for gates, fences and poles and even boats. Within the United States (US) alone concrete powers a US$35 billion construction industry, employing more than two million workers. More than 55,000 miles (89,000 km) of highways in the United States are paved with this material. Reinforced concrete, prestressed concrete and precast concrete are the most widely used types of concrete functional extensions.

Concrete is strong in compression, as the aggregate efficiently carries the compression load. However, it is weak in tension as the cement holding the aggregate in place can crack, allowing the structure to fail. Reinforced concrete solves these problems by adding steel reinforcing bars, steel fibers, glass fiber, or plastic fiber to carry tensile loads. Thereafter the concrete is reinforced to withstand the tensile loads upon it. Due to their low cost and wide availability steel reinforcing bar (commonly referred to as rebar) has been the dominant reinforcing material for the past 50 years. However, these steel rebars may corrode whereby the oxidation products (rust) expand and tend to flake, thereby cracking the concrete and reducing the bonding between the rebar and the concrete. Such corrosion may arise from several sources including carbonation when the surface of concrete is exposed to high concentration of carbon dioxide or chlorides, such as when the concrete structure is in contact with a chloride-contaminated environment such as arises with de-icing salts and marine environment.

Chlorides, including sodium chloride, contribute to the initiation of corrosion in embedded steel rebar if present in sufficiently high concentration. Chloride anions induce both localized corrosion (pitting corrosion) and generalized corrosion of steel reinforcements. Accordingly, the quality of water used for mixing concrete becomes important, as does ensuring that the coarse and fine aggregates do not contain chlorides, and nor do any admixtures contain chlorides. However, it was once common for calcium chloride to be used as an admixture to promote rapid setting of the concrete as it was also mistakenly believed to prevent freezing. However, this practice has fallen into disfavor once the deleterious effects of chlorides became known but a significant portion of existing concrete infrastructure employed calcium chloride. Additionally, the use of de-icing salts on roadways, used to reduce the freezing point of water, probably to date has been one of the primary causes of premature failure of reinforced or pre-stressed concrete bridge decks, roadways, and parking garages.

US bridges have been typically built to last 50 years. However, the average bridge in the US is now 47 years old. According to the U.S. Department of Transportation, of the 600,905 bridges across the country as of December 2008, 72,868 (12.1%) were categorized as structurally deficient and 89,024 (14.8%) were categorized as functionally obsolete. A structurally deficient bridge may be closed or restrict traffic in accordance with weight limits because of limited structural capacity. These bridges are not unsafe, but must post limits for speed and weight. A functionally obsolete bridge has older design features and geometrics, and though not unsafe, cannot accommodate current traffic volumes, vehicle sizes, and weights. These restrictions not only contribute to traffic congestion, they also cause such major inconveniences as forcing emergency vehicles to take lengthy detours and lengthening the routes of school buses.

With truck miles nearly doubling over the past 20 years and many trucks carrying heavier loads, the spike in traffic is a significant factor in the deterioration of bridges. Of the more than 3 trillion vehicle miles of travel over bridges each year, approximately 223 billion miles come from trucks. Accordingly, with the legal maximum weight of truck being 40 tons compared to an average car of 2 tons trucks account for approximately 9 trillion ton-miles of loading to bridges whilst cars account for approximately 5.5 trillion ton-miles.

Whilst road and railway bridges are highly visible occurrences of structural degradations from corrosion of rebar concrete structures these reinforced structures form the basis of common building foundations, buildings, footbridges, sewage systems, etc. Accordingly, determining corrosion within rebar concrete structures has been a focus of research and development for many years and issued testing standards with particular emphasis on electrical resistivity measurements within the laboratory from samples taken from structures.

Corrosion is an electro-chemical process. Accordingly, the flow rate of the ions between the anode and cathode areas, and therefore the rate at which corrosion can occur, is affected by the resistivity of the concrete. Empirical tests comparing electrical resistivity measurements with other physical and chemical analysis have generated the threshold values given by Equations (1) through (3) below as determining the likelihood of corrosion.

$$\rho > 120 \ \Omega \cdot m \ \text{corrosion is unlikely} \quad (1)$$

$$80 \ \Omega \cdot m \leq \rho \leq 120 \ \Omega \cdot m \ \text{corrosion is possible} \quad (2)$$

$$\rho < 80 \ \Omega \cdot m \ \text{corrosion is fairly certain} \quad (3)$$

These values have to be used cautiously as there is strong evidence that chloride diffusion and surface electrical resistivity is dependent on other factors such as mix composition and age. Further, the electrical resistivity of the concrete cover layer decreases due to increasing concrete water content, increasing concrete porosity, increasing temperature, increasing chloride content, and decreasing carbonation depth. However, as an overall industry rule when the electrical resistivity of the concrete is low, the rate of corrosion increases. When the electrical resistivity is high, e.g. in case of dry and carbonated concrete, the rate of corrosion decreases.

Laboratory based measurements of electrical resistivity may exploit two electrode methods wherein the concrete electrical resistance is measured by applying a current using two electrodes attached to the ends of a uniform cross-section specimen and electrical resistivity calculated. This method suffers from the disadvantage that contact resistance can significantly add to the measured resistance causing inaccuracy. Accordingly, this can be overcome by using four electrodes wherein a pair of outer electrodes is used to inject current as before, but the voltage is measured between a second pair of inner electrodes. The effective length of the sample being measured is the distance between the two inner electrodes. Less commonly employed is a transformer to measure resistivity without any direct contact with the specimen. The transformer consists of a primary coil which energises the circuit with an AC voltage and a secondary which is formed by a toroid of the concrete sample.

On-site electrical resistivity of concrete is commonly measured using four probes in a Wenner array which is used for the same reason as in the laboratory methods, namely to overcome contact errors. In this method four equally spaced probes are applied to the specimen in a line. The two outer probes induce the current to the specimen and the two inner electrodes measure the resulting potential drop. The probes are all applied to the same surface of the specimen and the method is consequently suitable for measuring the resistivity of bulk concrete in situ.

However, it would be evident that 600,000 concrete bridges with their associated support piers together with 55,000 miles of concrete road surface and billions of tons of concrete in buildings represent a significant measurement hurdle in terms of establishing protocols for rapid testing as well as associating the measurements specifically to particular elements of the physical infrastructure being evaluated. Accordingly, it would be beneficial for a field characterization system to automatically triangulate the location of the electrical resistivity device so that mapping of a structure can be performed without requiring an initial mapping of the structure to define measurement locations. It would be evident that erroneous association of electrical resistivity measurements to the wrong section of a structure may result in substantial disruption, such as closing the wrong side of a bridge to perform repairs where it then becomes evident the other side was actually corroding as the repairs having destroyed the road surface to get to the rebars find them non-corroded. Further, such erroneous activities substantially increase the overall costs of performing repairs straining already limited Federal and State budgets for example.

In other circumstances the concrete may have been covered with asphalt as a result of road resurfacing, repairs, etc. Accordingly, there is the problem of making quick and reproducible contact to the concrete through these overlying materials. It would therefore be beneficial to provide a means of improving this contact in such a manner. Likewise, it is the low frequency impedance of rebar in concrete that is correlated to the corrosion state of the steel reinforcement rods within the concrete. Accordingly, the direct measurement of the low frequency impedance of the rebar is a very time consuming measurement and one that is vulnerable to noise. As such, this low frequency technique is not easy to use in the field which is why commercial prior art electrical resistivity meters employ AC measurements of electrical resistivity at certain high enough frequencies. Hence, it would be beneficial to provide a means of making the electrical resistivity measurements that allows the low frequency resistivity to be derived from the measurements thereby improving determination of corrosion whilst reducing measurement times.

Likewise, prior art techniques for measuring the electrical resistivity of rebar, such as half-cell potential measurements, require that electrical connection is made to the rebar in contrast to concrete electrical resistivity measurements that determine the properties of the concrete surrounding the rebar. Accordingly, this requirement increases the complexity of making the measurements and requiring additional disruption/repair/cost even when no corrosion is identified. However, in many instances this is not feasible such as with epoxy coated steel rebar which is intended to reduce the occurrences of corrosion but as the rebars are electrically isolated from each other half-cell potential measurements are infeasible. As such it would be beneficial to provide a method of determining the state of rebar without requiring an electrical contact to the rebar with in the concrete infrastructure.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention to address limitations within the prior art relating concrete testing and more particularly to electrical methods and systems for measuring corrosion of rebar in reinforced concrete structures.

In accordance with an embodiment of the invention there is provided a method comprising:
providing an electrical measurement system for measuring an electrical characteristic of a concrete structure;
providing at least one beacon of a plurality of beacons, each beacon including a predetermined portion of a transceiver providing pulses of a predetermined format;
providing a global positioning system to provide a global position;
performing an electrical measurement of the electrical characteristic of a concrete structure;
determining at least a relative location of a plurality of relative locations, each relative location being that of the electrical measurement system relative to a predetermined subset of the plurality of beacons; and
storing the electrical measurement together with the plurality of relative locations and the global position.

In accordance with an embodiment of the invention there is provided a method comprising:
drilling a hole through the thickness of a covering to a layer of concrete forming a predetermined portion of a concrete structure;
filling the hole with a fluid which is electrically conductive;
connecting one end of an electrical measurement system for measuring an electrical characteristic of a concrete structure to the fluid and the other end to another part of the concrete structure; and
performing the electrical measurement.

In accordance with an embodiment of the invention there is provided a method comprising:
providing an electrical measurement system for measuring an electrical characteristic of a concrete structure;
generating with the electrical measurement system an electrical pulse which is applied to a first part of the concrete structure;
measuring with the electrical measurement system an output electrical signal with a probe applied to a second part of the concrete structure, the output electrical signal being the result of application of the electrical pulse to the first part of the concrete structure;
applying a predetermined signal processing algorithm to the output electrical signal to generate a low frequency electrical characteristic of the concrete structure.

In accordance with an embodiment of the invention there is provided a method comprising:
providing an electrical measurement system for measuring an electrical characteristic of a predetermined portion of concrete structure, the electrical measurement system comprising at least four probes, the inner pair of probes having a first predetermined spacing and the outer pair of probes having a second predetermined spacing;
generating with the electrical measurement system a plurality of applied electrical currents which are applied to a first part of the concrete structure via the outer pair of probes, the plurality of applied electrical currents being at a series of predetermined frequencies from a predetermined lower frequency limit to a predetermined upper frequency limit;
measuring with the electrical measurement system a plurality of output electrical voltages with the inner pair of probes, each of the plurality of output electrical voltages being at one of the predetermined frequencies;
applying a predetermined signal processing algorithm to the plurality of output electrical voltages to generate a frequency dependent electrical characteristic of the predetermined portion of concrete structure; and
determining an indication of corrosion for the predetermined portion of concrete structure in dependence upon at least the frequency dependent electrical characteristic.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 4A depicts a system configuration for automatic location mapping of electrical measurements according to an embodiment of the invention;

DETAILED DESCRIPTION

The present invention is directed to concrete testing and more particularly to electrical methods and systems for measuring rebar corrosion in reinforced concrete structures The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing an exemplary embodiment. It being understood that various changes may be made in the function and arrangement of elements without departing from the spirit and scope as set forth in the appended claims.

A "portable electronic device" (PED) as used herein and throughout this disclosure, refers to a wireless device that requires a battery or other independent form of energy for power. This includes devices including, but not limited to, cellular telephone, smartphone, personal digital assistant (PDA), portable computer, pager, portable multimedia player, portable gaming console, laptop computer, tablet computer, and an electronic reader.

A "fixed electronic device" (FED) as used herein and throughout this disclosure, refers to a wired and/or wireless device used which is dependent upon a form of energy for power provided through a fixed network, e.g. an electrical mains outlet coupled to an electrical utilities network. This includes devices including, but not limited to, portable computer, desktop computer, computer server, Internet enabled display, mainframe, and server cluster. Such PEDs and FEDs supporting one or more functions and/or applications including, but not limited to, data acquisition, data storage, data analysis, communications, and Internet/Web interface.

Figure 1:
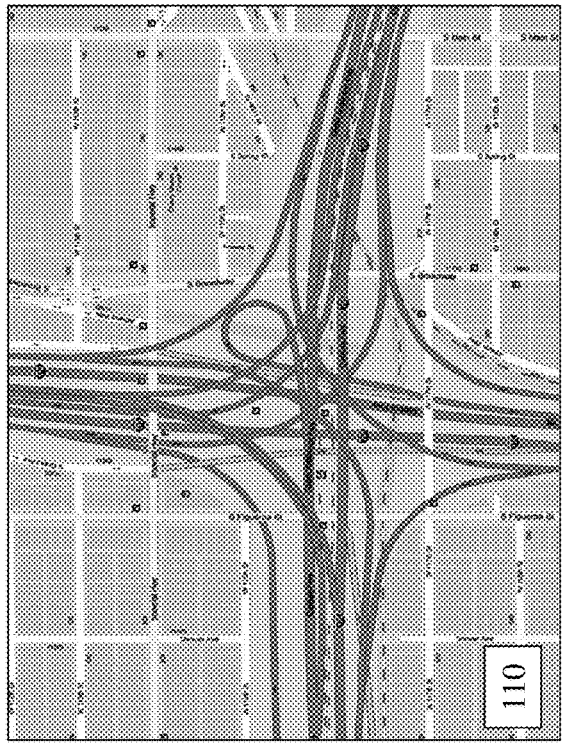
FIG. 1 depicts examples of concrete infrastructure that require characterization as well as rebar reinforced concrete.
Figure 1:
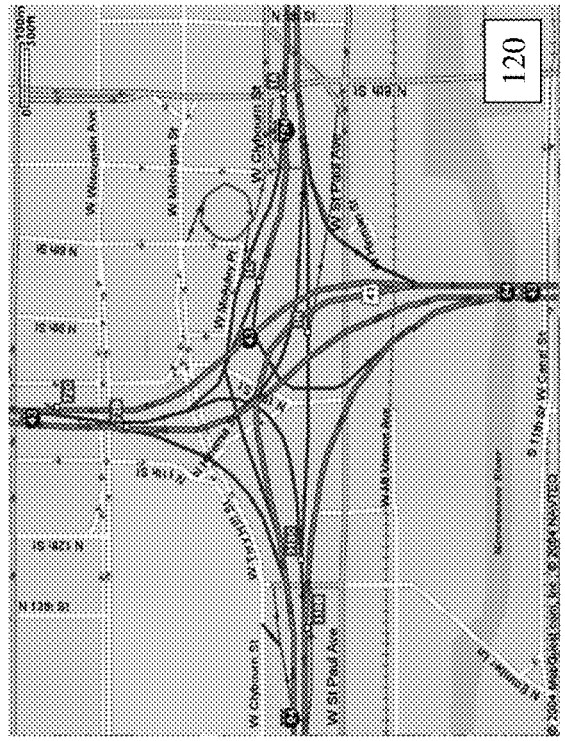
Figure 1:
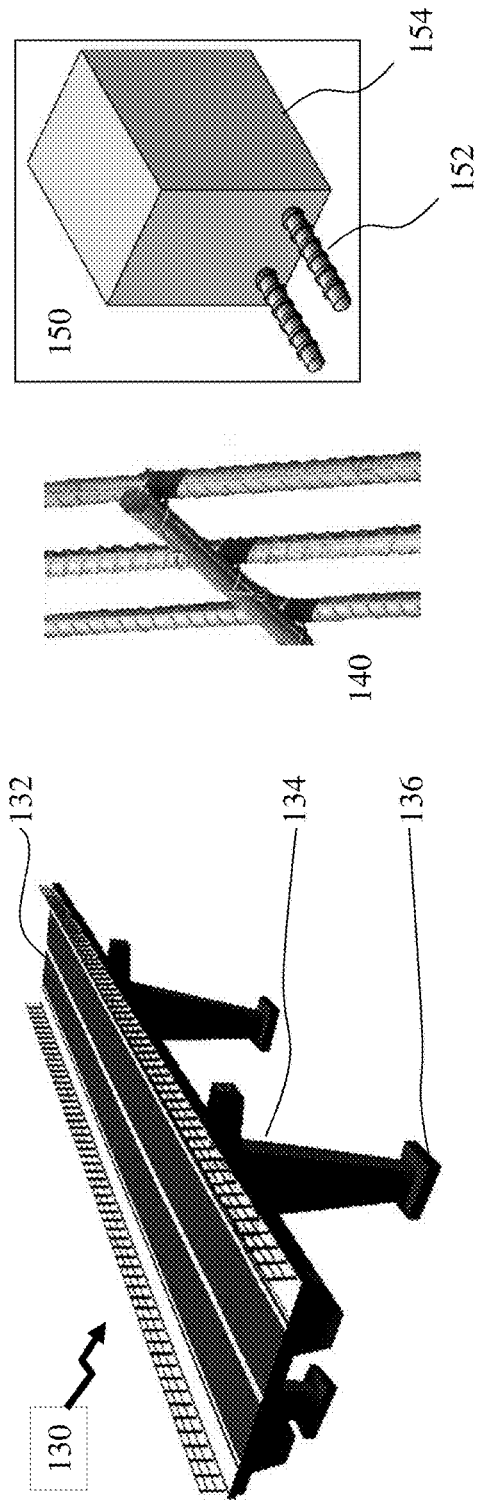

Referring to FIG. 1 there are depicted first and second concrete infrastructures 110 and 120 which are the "Highway #1 Intersection 105 & 110" in Los Angeles, USA and "Marquette" Interchange in Milwaukee, USA respectively. Whilst perhaps overly dramatic these are just two of the 600,000 bridges and millions of buildings in the US requiring characterization for corrosion. These numbers represent just a fraction of those globally which require measurements to determine the corrosion levels of these infrastructure elements on a periodic basis.

Bridge structure 130 is a schematic of a bridge showing the road surface 132 together with supports 134 and foundation 132. All of these elements require characterization during the lifetime of the bridge structure 130 but typically the road surface 132 will be tested more frequently in areas where salt and other chemicals are used to address snow and ice on the surface during winter. Rebar schematic 140 shows a typical rebar configuration for reinforcing concrete wherein long rebar rods are employed along the axis experience tensile loading where their positions relative to each other prior to concrete pour are maintained through tying another rods periodically along them as well as supporting these within the frame work into which the concrete will be poured to surround the rebars and form the concrete infrastructure. A schematic of such a structure is depicted in schematic 150 wherein the rebars 152 are embedded in the concrete 154.

Figure 2:
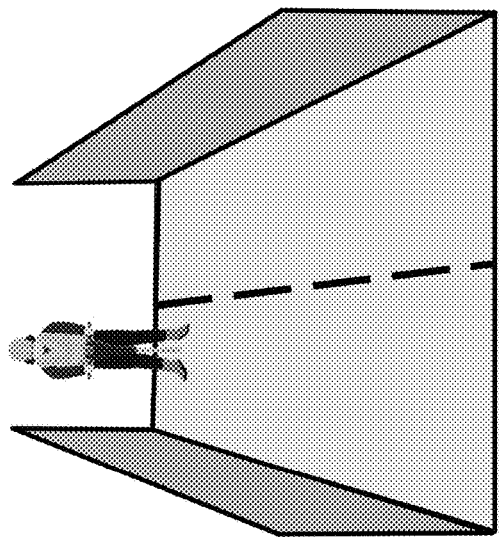
FIG. 2 depicts surface electrical resistivity measurements and embedded resistance probes according to the prior art.
Figure 2:
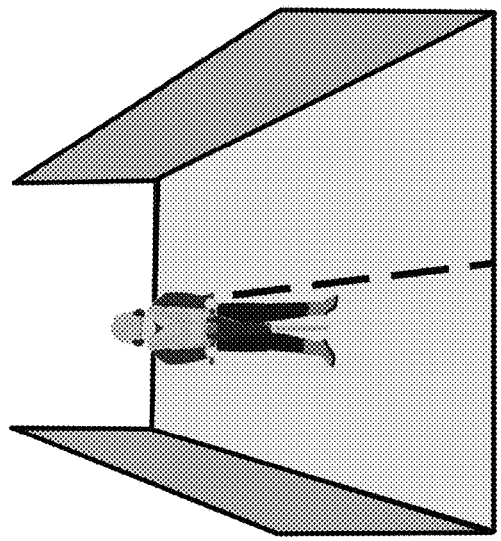
Figure 2:
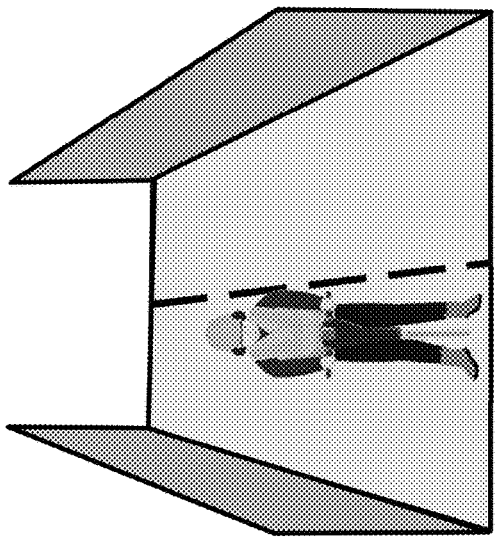
Figure 2:
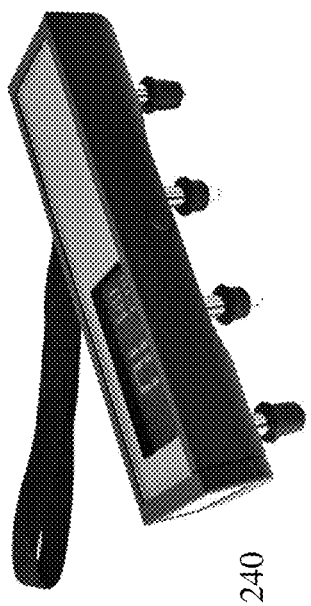
Figure 2:
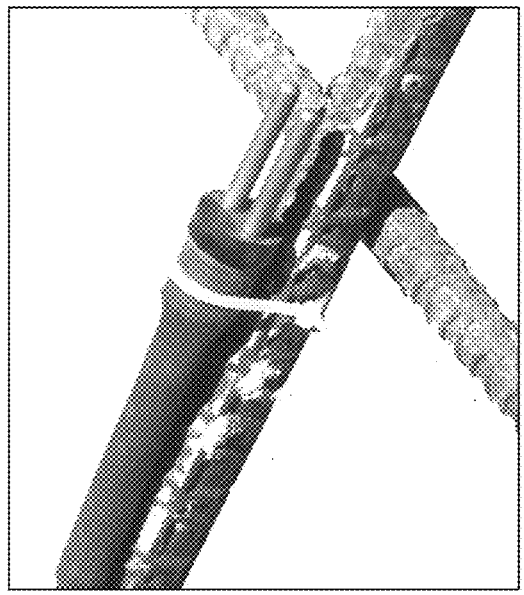

Now referring to FIG. 2 there are depicted first to third images 210 through 230 respectively of surface electrical resistivity measurements according to the prior art. First to third images 210 through 230 respectively show a worker walking across a road surface performing measurements wherein they walk one pace, stop, make a measurement, walk another pace, stop, make a measurement. There is no reference to their position along the road surface and their position across the road whilst defined by the eroded white line at this point will be lost when the road surface is resurfaced, repainted, etc. Accordingly, these measurements are isolated, discrete measurements that cannot be correlated to any subsequent measurements taken in 1, 2, 3, or 5 years time for example to determine structure changes. Equally, the data when taken away and analysed identifies an area of corrosion requiring correction through physical intervention. A work crew returning may be addressing a small area but without alignment to the physical structure the measurements provide no additional benefit and accordingly it is likely that the physical intervention will involve a substantial portion of the road surface. Likewise, a simple error in denoting which side of the road the measurements were made on results in the wrong side of the road surface being ripped up.

Fourth image 240 depicts a four-point Wenner probe as employed in surface electrical resistivity measurements such as those made by the worker in first to third images 210 through 230 respectively. It applies a 40 Hz AC electrical current from the outer pair of electrodes and measures the voltage between the inner pair of electrodes which is then converted to an electrical resistivity displayed on the screen and in the instance of first to third images 210 through 230 manually entered into a portable device by the work. Alternatively, rather than onsite measurements through such Wenner probes as depicted in fourth image 240 another approach is to exploit embedded sensors such as the one depicted in fifth image 250 may be employed. The probe depicted is a CORRATER Model 800 probe from Rohrback Cosasco Systems that measures the instantaneous corrosion rate of reinforcing steel in concrete by the method of linear polarization resistance (LPR). Each reading gives the instantaneous corrosion rate of the electrodes in the concrete environment, and the probes are monitored frequently or continuously to track changes in corrosion rate. However, these embedded sensors are expensive individually and deploying a matrix of them across say even a 100 m×10 m bridge prohibitive even without considering the additional complexities of interface cabling, measurement electronics etc. Accordingly, such embedded sensors tend to be used infrequently.

Figure 3:
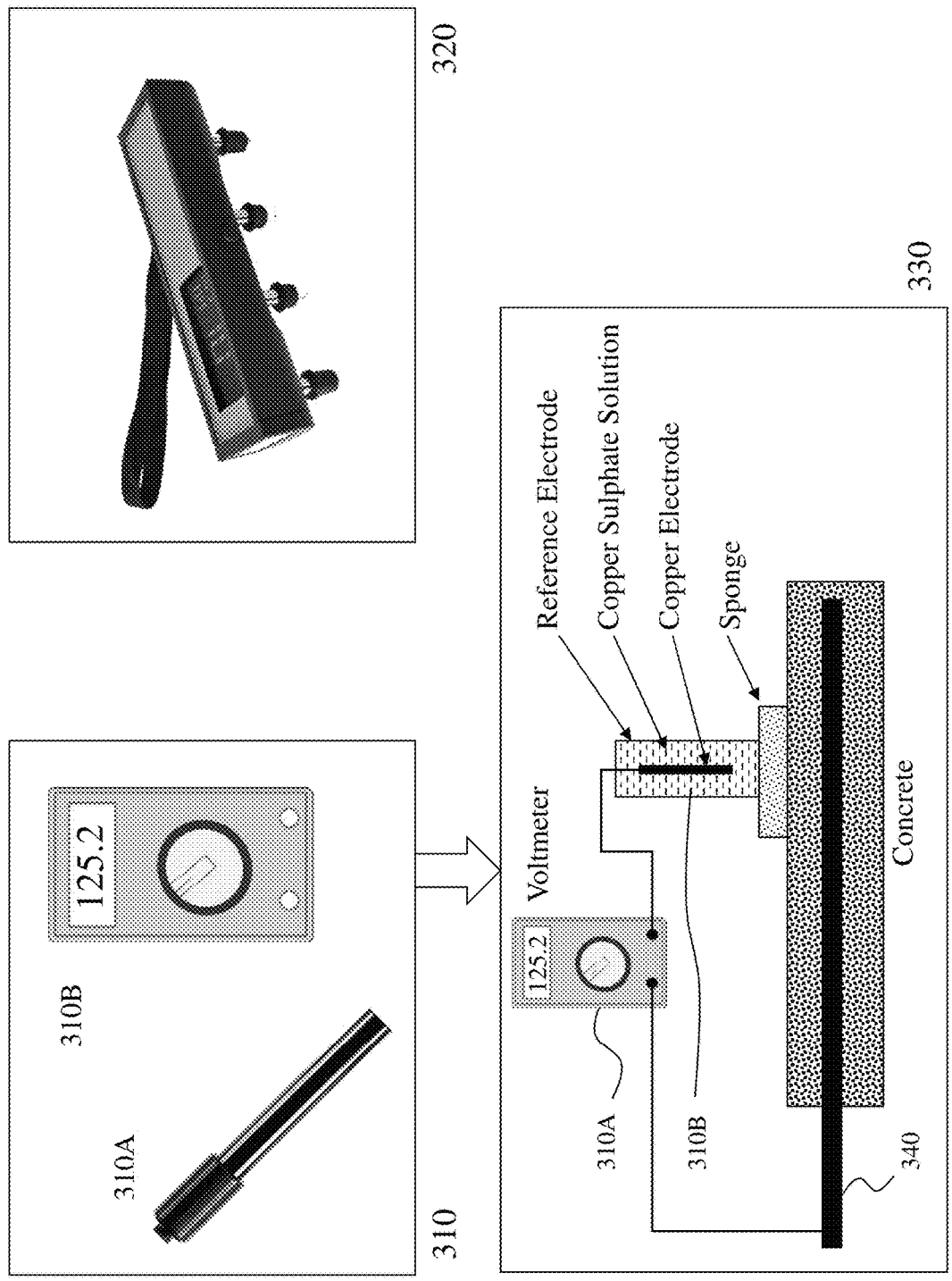
FIG. 3 depicts half-cell potential and surface resistivity measurements according to the prior art.

Referring to FIG. 3 there are depicted half-cell potential meter 310 and surface resistivity meter 320 equipment according to the prior art. Half-cell potential meter 310 comprises a half-cell 310A and multimeter 310B which are depicted in deployment 330 are connected to each other via an interconnection cable. The other side of the multimeter 310A is electrically connected to the rebar 340 such that the electrical circuit for the multimeter 310A is completed via the rebar 340, the concrete and the half-cell 310A. Electrical contact of the half-cell 310A to the concrete is facilitated typically by the use of a wet sponge. As corrosion of reinforcing steel is an electro-chemical process then the behaviour of the steel can be characterized by measuring its half-cell potential where the greater the potential the higher the risk that corrosion is taking place. An electrode forms one half of the cell and the reinforcing steel in the concrete forms the other. A common reference electrode for site use is silver/silver chloride in potassium chloride solution although the copper/copper sulphate electrode is still widely used. It should be noted that the measured potential should be corrected relatively based on the type of electrode employed, concentration of electrochemical half-cell 310A, pressure, and the temperature of the measurement. The survey procedure is firstly to locate the steel and determine the bar spacing using a cover meter, then the cover concrete is removed locally over a suitable bar and an electrical connection made to the steel. It is necessary to check that the steel is electrically continuous by measuring the resistance between two widely separated points. The reinforcing bar is connected to the half-cell via the multimeter 310B. Accordingly, this is a time consuming process and mapping subject to the same issues as discussed supra in respect of FIG. 2 for the Wenner probe such as depicted in FIG. 3 by surface resistivity meter 320.

Due to the limitations of the prior art approaches mapping of concrete structures has typically been ad-hoc and limited to small numbers of measurements. For example, "Test Method WA 622.1 Resistivity of Concrete" (issued by Materials and Pavement Technology of Main Roads Western Australia), describes a procedure for single spot measurements with no consideration of where they are to be taken. Whilst limited mapping results are presented within the literature these have been as the result of research activities on single structures usually with academic researchers who are able to take the time to mark out a matrix of measurements and then sequentially perform them, see for example Gucunski et al in "Nondestructive Testing to Identify Concrete Bridge Deck Deterioration" (American Association of State Highway and Transportation Officials, 2012 Subcommittee on Bridges and Structures Meeting, Austin, Tex.) which was the result of a US$750 k research project led by Rutgers University.

It would be evident that it would be beneficial to provide devices and systems allowing for increased use of electrical resistivity mapping on concrete infrastructure as well as improving the correlation of subsequent measurements spatially to improve the accuracy of the mapping and also track elements within the structure over time.

Now referring to FIG. 4A there is depicted a system configuration for automatic location mapping of electrical measurements according to an embodiment of the invention. Whilst the embodiments of the invention are described primarily from the viewpoint of electrical measurements it would evident that the techniques may be applied to other test measurements, concrete test measurements, and other non-destructive tests (NDTs). Depicted are half-cell potential system (HCPS) 410 and surface electrical resistivity system (SERS) 420 as discrete devices and as first and second systems 430 and 440 respectively. In first system 430 the half-cell 410A and multimeter 410B are connected as previously described in respect of FIG. 3 and the electrical circuit is completed with the connection to the rebar. However, multimeter 410B is now in communication with a tablet PC 450 via an interface 460. The tablet PC 450 is also in communication with first and second beacons 470A and 470B which contain a GPS receiver and ultrasonic/radio frequency transmitter together with a wireless interface, not shown for clarity. Accordingly, the tablet PC 450 receives GPS data from each of the first and second beacons 470A and 470B as well as synchronizing the ultrasonic transducers. An ultrasonic receiver within multimeter 410B receives the ultrasonic signals from the ultrasonic transmitters allowing it to determine its distance from each of the first and second beacons 470A and 470B respectively. These distances are communicated to the tablet PC 450 allowing the location of each measurement to be automatically logged.

Likewise in second system 440 the SERS 420 is depicted as meter 480 and probes 490. The meter 480 is again in communication with the tablet PC 450 via an interface 460 whilst the tablet PC 450 similarly receives GPS data from the first and second beacons 470A and 470B respectively. Similarly the meter 480 contains an ultrasonic receiver such that the relative position of the meter relative to the first and second beacons 470A and 470B respectively can be determined. The addition of ultrasonic ranging, or another ranging technique, to augment the GPS location arises as the standard quoted accuracy of a low cost GPS receiver is approximately 15 meters (49 feet) and that even for high quality receivers according to the GPS Standard Positioning Service (SPS) it is currently approximately 3 meters (10 feet) (http://www.gps.gov/systems/gps/performance/accuracy/). However, with ranging the accuracy of location setting achieved by the inventors is less than 10 cm representing approximately two orders of magnitude improvement over GPS and other local positioning systems (LPS) based upon wireless signal triangulation, radio broadcast tower triangulation, and imaging with accuracies of the order of a meter.

It would be evident that in operation first and second systems 430 and 440 respectively would typically employ 3 beacons to remove ambiguities over position whilst they are described as having 2 beacons. Optionally, ultrasonic range determination may be replaced by other techniques including, but not limited to, visible optical, infrared optical, visible or infrared laser based optical, microwave, and radio frequency distance measurements. Optionally, other variants may include performing the distance determination within the beacons, obtaining GPS location from a GPS receiver within the meter, and that the connection between meter and tablet PC may be wireless as are the connections from the beacons to the tablet PC. Alternatively, the data logging, wireless interface etc may be integrated within the meter eliminating the requirement for the separate tablet PC. Optionally, only one beacon may contain a GPS circuit.

Optionally, the GPS location, which may be considered a reference in some circumstances from which the secondary locations of the measurements points are determined may be replaced by another method of establishing a reference on the structure, including but not limited to architectural structures, foundations, brick/block walls, pavements, bridges/overpasses, and motorways/roads. Alternative methods may include, local positioning systems (LPSs) employing wireless techniques in conjunction with cellular base stations, Wi-Fi access points, and radio broadcast towers for example, establishing a predetermined point such as established by techniques such as surveying etc, or a predetermined distinctive point such as marker embedded into the structure. Accordingly, measurements may be established according to embodiments of the invention with references which are intrinsically linked (i.e. forming part of) or extrinsically linked (i.e. not forming part of) the structure and/or area being characterised and analysed. As such techniques may include a global positioning system, wireless triangulation, wireless multilateration, surveying from a survey reference point, and surveying from a predetermined point on the concrete structure. In some embodiments of the invention an initial reference point may be established and physically identified for subsequent periodic inspections. With location accuracies below 10 cm exploiting ranging techniques by the inventors it would be evident that periodic inspections are now feasible with overlaying subsequent corrosion maps to the original measurements.

Figure 4B:
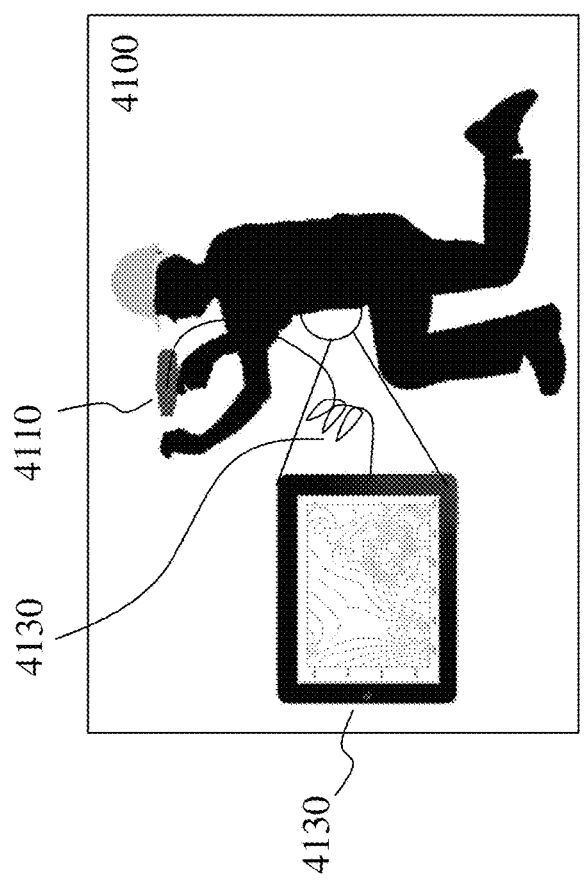
FIG. 4B depicts a system configuration for automatic location mapping of electrical measurements according to an embodiment of the invention.

Now referring to FIG. 4B there are depicted or configuration 4100 for automatic location mapping of electrical measurements according to an embodiment of the invention. As depicted in first configuration 4100 a user has a tablet 4120, upon a GoPad halter/holder, and a Giatec Cell™ 4110 which is a maintenance-free half-cell sensor that measures the corrosion potential and transmits this to the tablet for generating half-cell contour plots, i.e. corrosion maps 4400 in real-time. The user when making measurements can enter into the tablet 4120 which measurement they are making as depicted with entry grid 4300 wherein each measurement indicated as completed is denoted by a circle on the grid. Based upon the grid measurements made the corrosion map 4400 may be generated in real-time and shared in real-time with a remote engineering office through wireless communications of the tablet 4120 to a wireless network. Hence it would be evident that the Giatec Cell™ 4110 significantly reduces the labor cost associated with the data collection as well as simplifying and de-skilling it whilst automating the subsequent contour plot generation and reporting using software installed upon the tablet 4110. Giatec Cell™ 4110 includes a Bluetooth™ transceiver allowing the data to be sent to the tablet 4110 wirelessly. The cable 4130 represents the electrical connection to a rebar within the infrastructure such as described supra in respect of FIGS. 3 and 4A.

Figure 5:
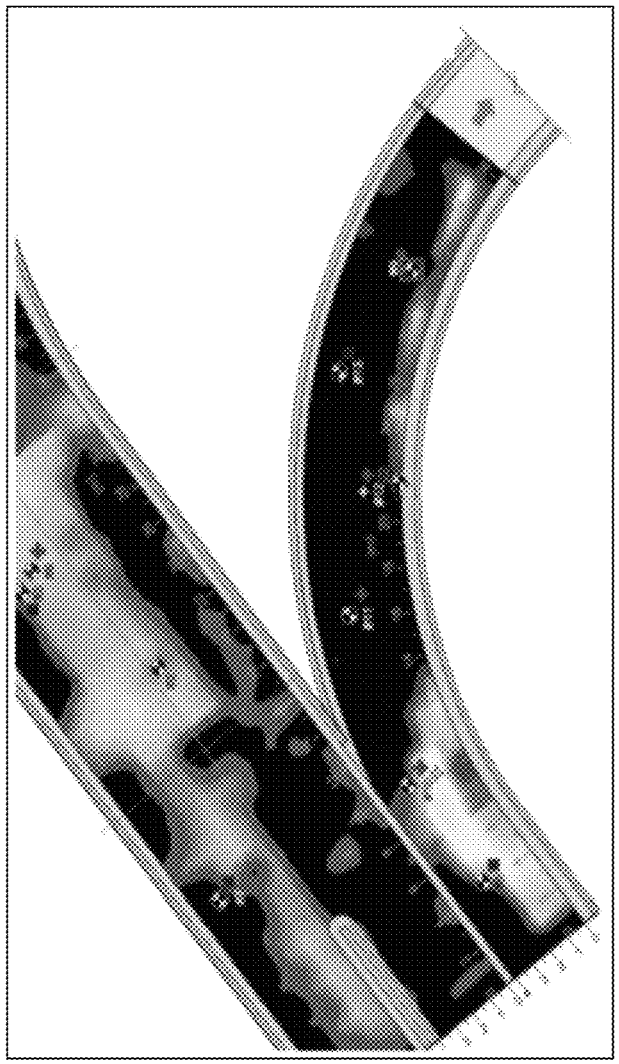
FIG. 5 depicts examples of concrete infrastructure mapping established according to embodiments of the invention.
Figure 5:
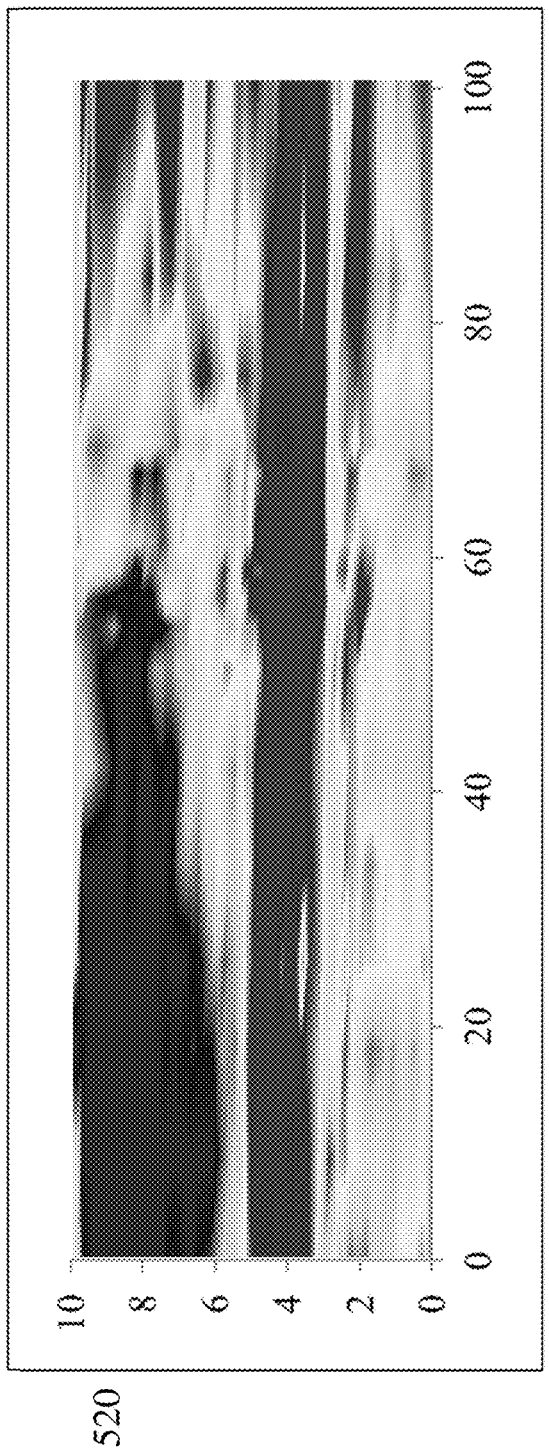

Accordingly, using a test system, such as one of first and second systems 430 and 440 respectively in FIG. 4A or configuration 4100 in FIG. 4B, an operator may establish a plurality of measurements across a concrete surface wherein the location of the test system is automatically determined relative to the beacons and a GPS location such that these results can then be processed to generate first and second contour maps 510 and 520 as depicted in FIG. 5. Accordingly, during testing an operator may perform measurements using a system such as described supra in respect of first and second systems 430 and 440 respectively in FIG. 4A or configuration 4100 in FIG. 4B in combination with the software upon the tablet 4110 which contains in addition to the software for managing the data acquisition and plotting data relating to the region or regions of an element of concrete infrastructure which is to be tested and present these sequentially to the user. Alternatively, the results from multiple test systems with multiple operators may be combined based upon the location data of the measurements. These multiple systems may operate with a single set of beacons or multiple test systems may be associated with multiple sets of beacons.

Figure 6A:
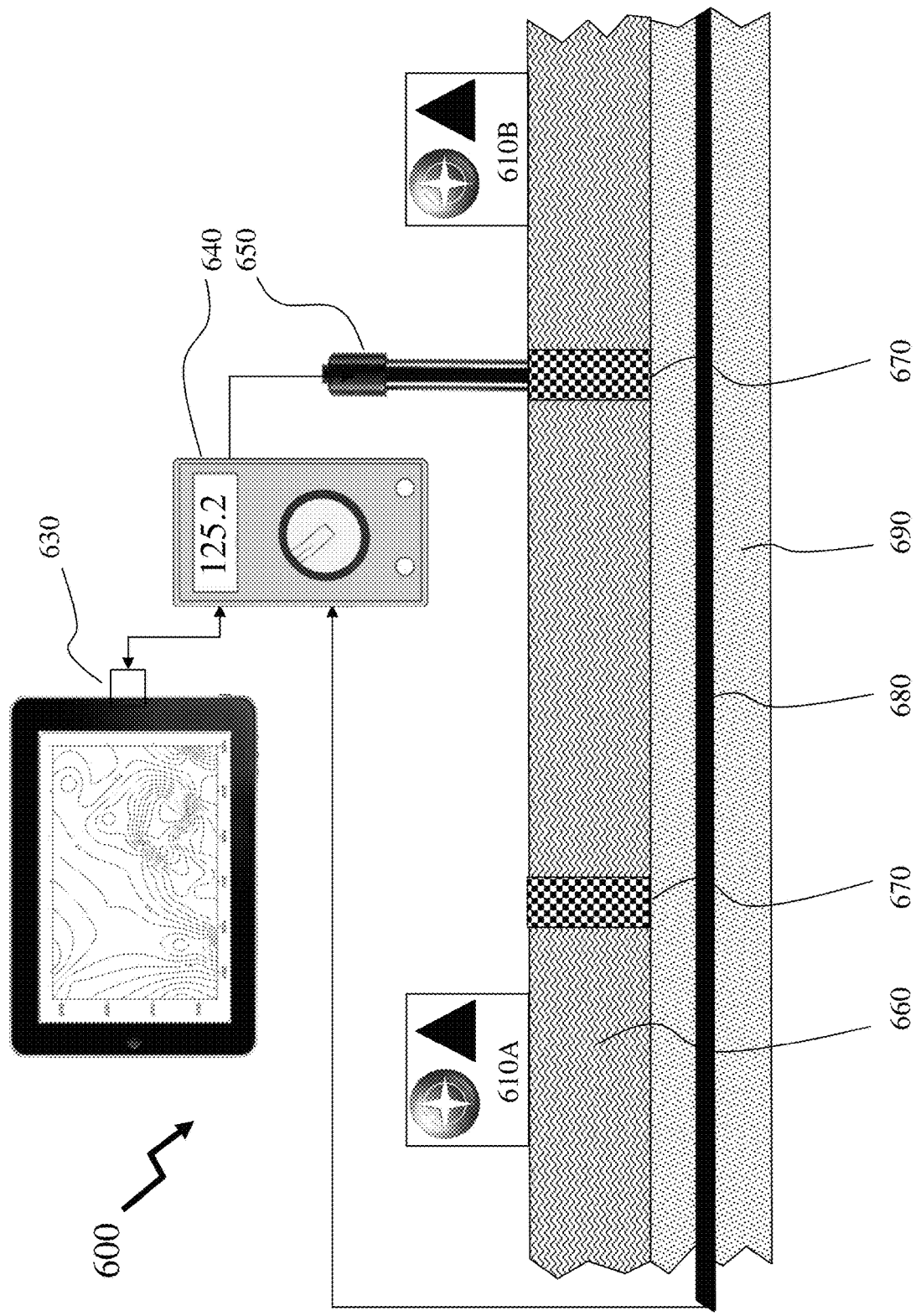
FIGS. 6A and 6B depict system configurations for automatic location mapping of electrical measurements according to an embodiment of the invention addressing the issue of asphalt or tarmac covered concrete.

Now referring to FIG. 6A there is depicted a system configuration 600 for automatic location mapping of electrical measurements according to an embodiment of the invention addressing the issue of asphalt or tarmac covered concrete. The measurement of steel corrosion potential inside concrete directly below the surface of an insulating material such as asphalt or tarmac is not possible. However, as evident in system configuration 600 the tablet PC 620 and interface 630 are coupled to the meter 640 and half-cell 650. Also depicted are first and second beacons 610A and 610B respectively. Also depicted are concrete 690, rebar 680, and asphalt 660. The technique comprises drilling holes 670 that drilled into the asphalt layer 660 to reach the surface of the concrete 690. These holes are then filled with a conductive gel or liquid to create an electrically conductive pathway from the half-cell 650 to the surface of the concrete allowing the corrosion potential of the rebar 680 to be measured. Accordingly, drilling multiple holes 670 allow for the mapping and/or discrete measurements on a concrete structure such as described supra in respect of FIGS. 4A to 5 respectively.

Figure 6B:
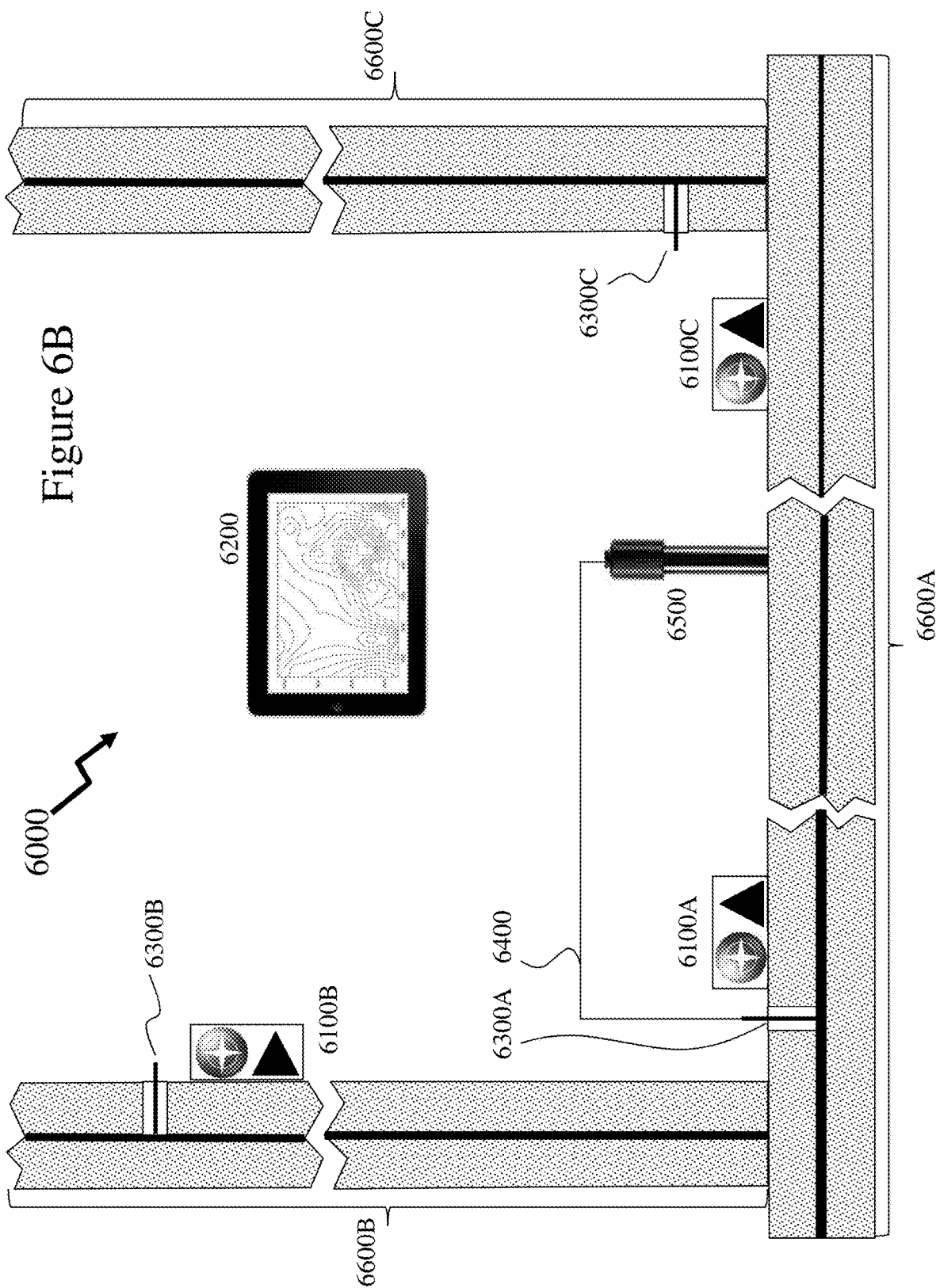

In contrast considering FIG. 6B there is depicted a system configuration 6000 for automatic location mapping of electrical measurements according to an embodiment of the invention. As depicted first to third infrastructure elements 6600A to 6600C with concrete and rebar construction are depicted within which first to third contacts 6300A to 6300C have been made to the rebars within. In respect of the rebar in the first infrastructure element 6600A the first contact 6300A is connected via cable 6400 to wireless half-cell 6500 wherein the resulting measurement is wirelessly transmitted to computer 6200. The position of wireless half-cell 6500 is established in dependence upon beacons 6100A to 6100C respectively which include both GPS and ultrasound elements although a combination of other optical, wireless, and microwave location and/or ranging techniques may be employed. Subsequently, prior to, or concurrent with measurements made with wireless half-cell 6500 its location is established in dependence upon at least first to third beacons 6100A to 6100C, and others potentially, such that the location of wireless half-cell 6500 is established in three-dimensions (3D) although as time is also established it may be considered as established in four-dimensions (4D) potentially. Accordingly, the wireless half-cell 6500 may depending upon which of first to third contacts 6300A to 6300C it is contacted to perform measurements upon first to third infrastructure elements 6600A to 6600C wherein based upon first to third beacons 6100A to 6100C and others, not shown for clarity, the 3D position of the wireless half-cell 6500 may be determined and its measurements communicated to computer 6200 for storage and/or communication via a network to a remote storage and/or analysis location. Through repeated measurements the first to third infrastructure elements 6600A to 6600C may be characterised with 3D mapping with the accuracy of 10 cm or less based upon the combination, for example, of ultrasound ranging with GPS location.

Figure 7:
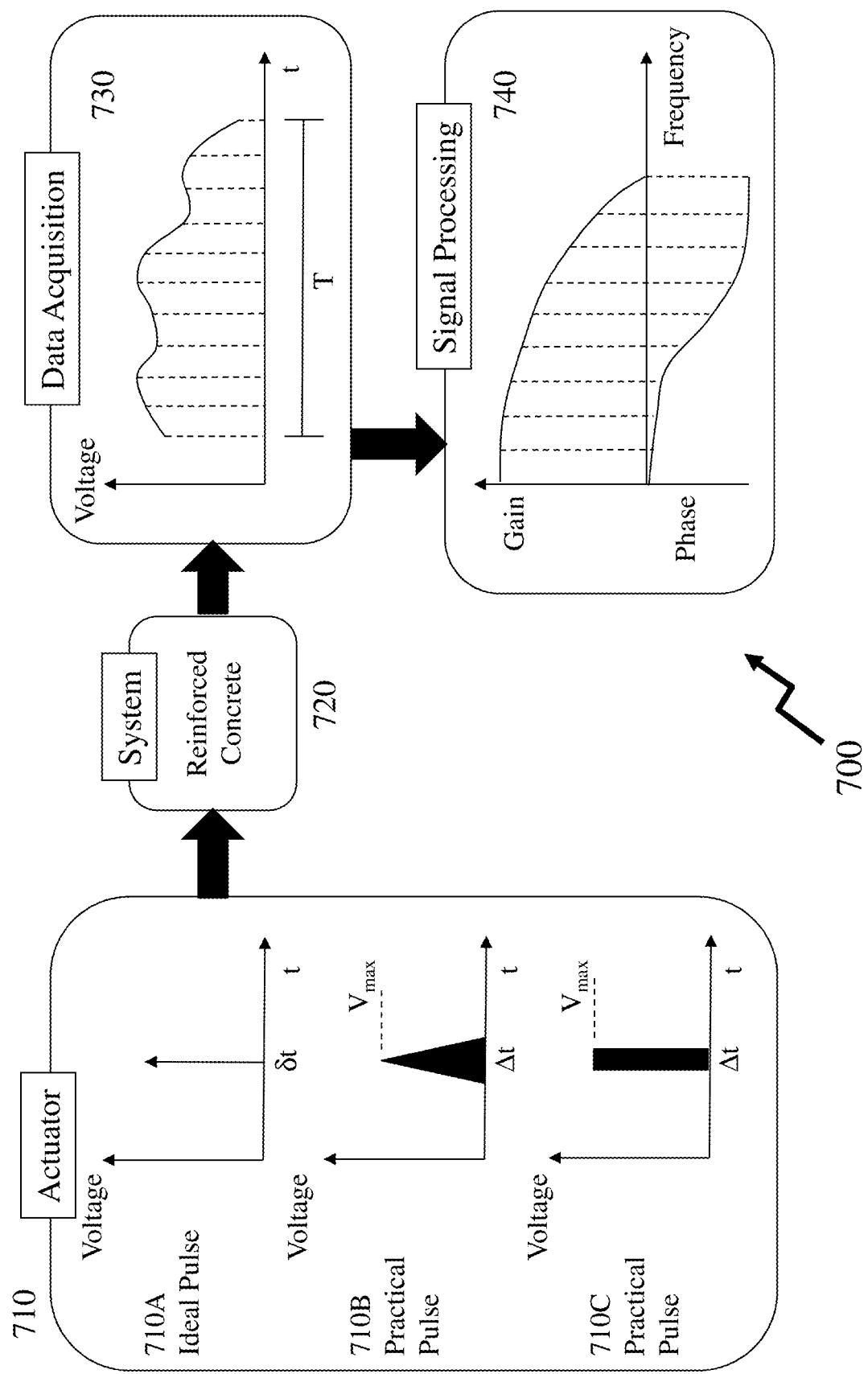
FIG. 7 depicts a schematic of pulsed electrical measurements according to an embodiment of the invention.

The low-frequency impedance of rebar in concrete can be correlated to the corrosion state of reinforcement in concrete. However, direct measurement of the low-frequency impedance of rebar in concrete is very time-consuming and vulnerable to noise interruption as discussed supra; hence it is not practical to use this technique in the field to measure the corrosion rate of rebar inside the concrete. Accordingly, within this innovative technique, the low-frequency behaviour of the steel rebar contact surface is determined by applying a narrow DC current pulse, or a DC step voltage, for a short period of time and recording the voltage of the system with a very high sampling rate. The highly sampled recorded voltage change is then processed to determine the low-frequency impedance of the rebar in concrete, which can be used to determine the state of corrosion in reinforced concrete structures. This process is schematically shown in FIG. 7 wherein a first step, the actuator 710, is depicted as ideal pulse 710 together with first and second practical pulses 710B and 710C respectively, which is then applied to the reinforced concrete. The resulting output voltage profile is depicted in data acquisition step 730 together with the subsequent signal processing step 740 wherein plots of gain and phase versus frequency, for example, are derived as a function of frequency allowing the low frequency characteristics of the rebar in concrete to be determined.

According to other embodiments of the invention a single pulse may be applied to multiple rebar elements simultaneously and received with multiple detectors disposed across the concrete structure being characterized. Optionally, the current pulse may be induced into the rebar without electrical contact through electromagnetic induction for example.

Figure 8:
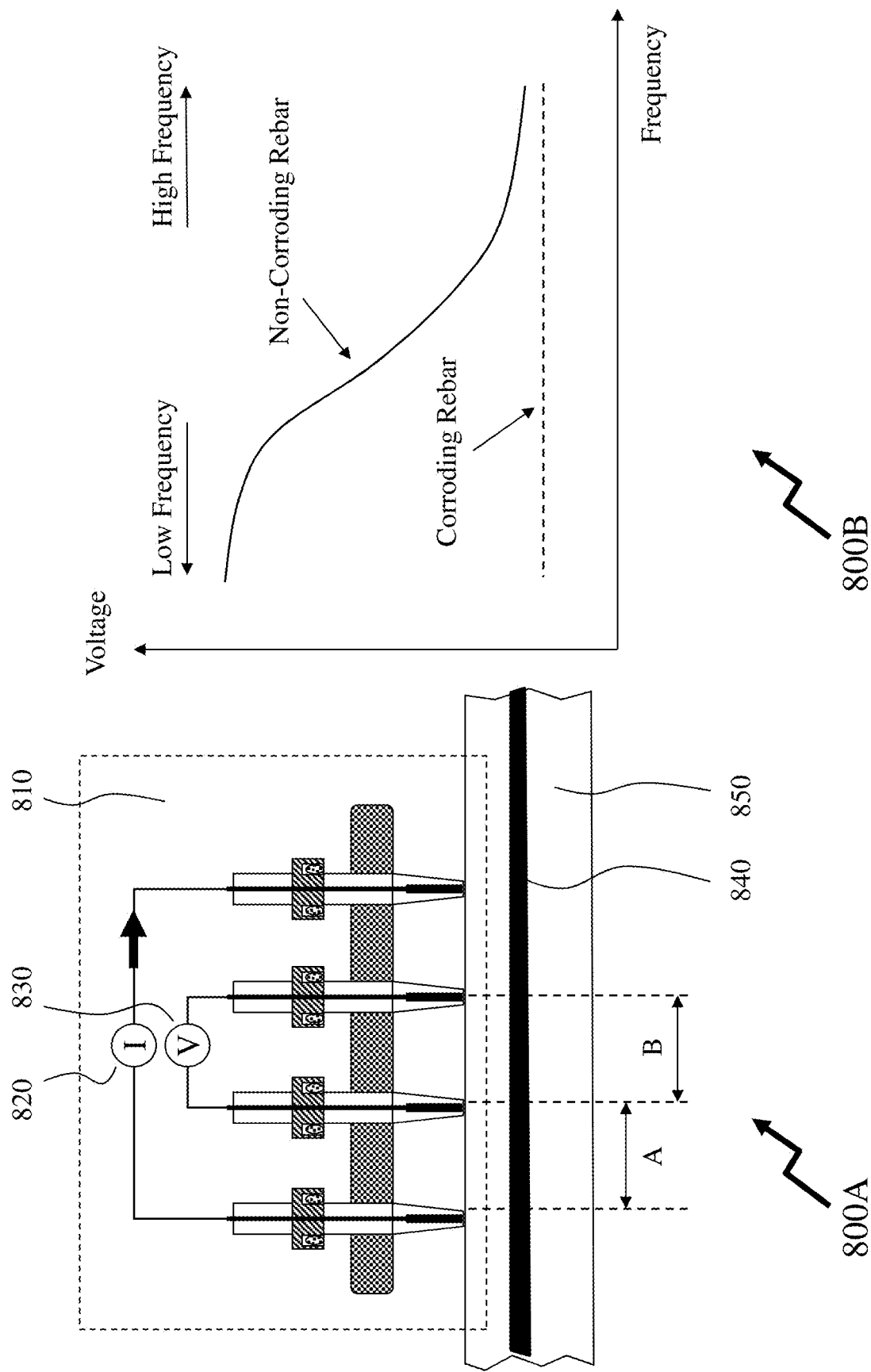
FIG. 8 depicts electrical characterization of a rebar within concrete without electrical connection to the rebar according to an embodiment of the invention.

FIG. 8 depicts electrical characterization of a rebar within concrete without electrical connection to the rebar according to an embodiment of the invention wherein the electrical response of rebar inside the concrete is determined from the surface of the concrete with four probes as shown in first image 800A of FIG. 8. A constant AC current is applied between the outer probes and the voltage between the inner probes is measured, such as discussed supra in respect of prior art 4-point Wenner probes for surface electrical resistivity measurements which operate at a single frequency, for example 40 Hz. However, the inventors have found that by sweeping the frequency of the AC current from high frequency to low frequency and recording the voltage of the measurement system, as illustrated schematically in second image 800B in FIG. 8, that the voltage response of the corroding rebar is different from that of a non-corroding rebar.

As depicted the voltage for a non-corroding rebar varies decreasing from the low frequency zone of the plot towards the high frequency zone, but it is almost invariable for the corroding rebar. Accordingly, using a swept frequency AC source and a fast voltage measurement system it is possible to detect the corroding areas of the reinforced concrete structures from the surface of the concrete with no requirement to provide have an electrical connection to the rebar inside the concrete, unlike other prior art non-destructive test techniques.

Figure 9:
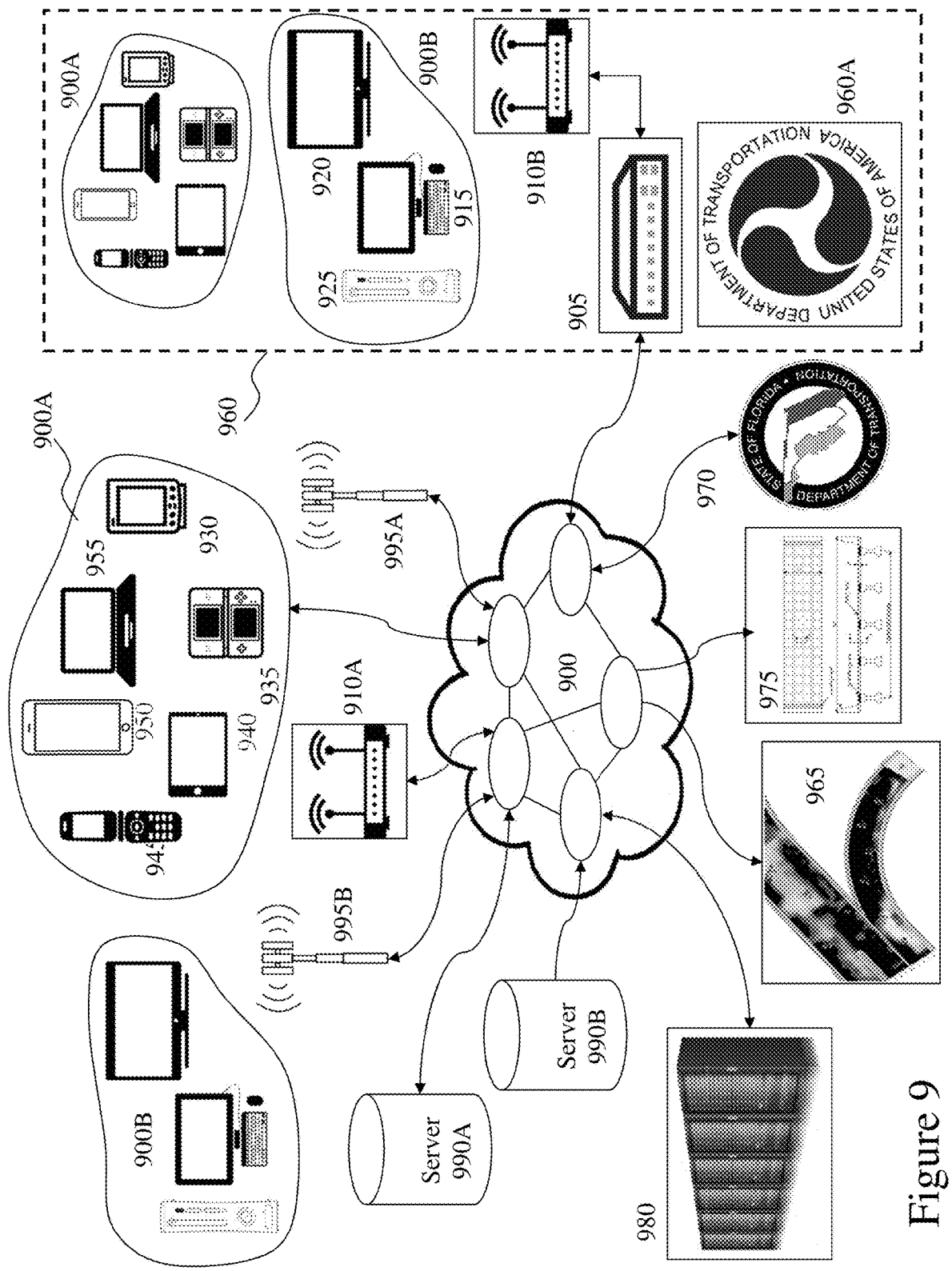
FIG. 9 depicts a network supporting communications to and from electronic devices implementing contextual based UIs according to embodiments of the invention.

Now referring to FIG. 9 there is depicted a network 900 supporting communications to and from electronic devices implementing contextual based UIs according to embodiments of the invention. As shown first and second user groups 900A and 900B respectively interface to a telecommunications network 900. Within the representative telecommunication architecture a remote central exchange 980 communicates with the remainder of a telecommunication service providers network via the network 900 which may include for example long-haul OC-48/OC-192 backbone elements, an OC-48 wide area network (WAN), a Passive Optical Network, and a Wireless Link. The central exchange 980 is connected via the network 900 to local, regional, and international exchanges (not shown for clarity) and therein through network 900 to first and second wireless access points (AP) 995A and 995B respectively which provide Wi-Fi cells for first and second user groups 900A and 900B respectively. Also connected to the network 900 are first and second Wi-Fi nodes 910A and 910B, the latter of which being coupled to network 900 via router 905. Second Wi-Fi node 910B is associated with Government Body 960A and environment 960 within which are first and second user groups 900A and 900B. Second user group 900B may also be connected to the network 900 via wired interfaces including, but not limited to, DSL, Dial-Up, DOCSIS, Ethernet, G.hn, ISDN, MoCA, PON, and Power line communication (PLC) which may or may not be routed through a router such as router 905.

Within the cell associated with first AP 910A the first group of users 900A may employ a variety of portable electronic devices including for example, laptop computer 955, portable gaming console 935, tablet computer 940, smartphone 950, cellular telephone 945 as well as portable multimedia player 930. Within the cell associated with second AP 910B are the second group of users 900B which may employ a variety of fixed electronic devices including for example gaming console 925, personal computer 915 and wireless/Internet enabled television 920 as well as cable modem 905.

Also connected to the network 900 are first and second APs which provide, for example, cellular GSM (Global System for Mobile Communications) telephony services as well as 3G and 4G evolved services with enhanced data transport support. Second AP 995B provides coverage in the exemplary embodiment to first and second user groups 900A and 900B. Alternatively the first and second user groups 900A and 900B may be geographically disparate and access the network 900 through multiple APs, not shown for clarity, distributed geographically by the network operator or operators. First AP 995A as show provides coverage to first user group 900A and environment 960, which comprises second user group 900B as well as first user group 900A. Accordingly, the first and second user groups 900A and 900B may according to their particular communications interfaces communicate to the network 900 through one or more wireless communications standards such as, for example, IEEE 802.11, IEEE 802.15, IEEE 802.16, IEEE 802.20, UMTS, GSM 850, GSM 900, GSM 1800, GSM 1900, GPRS, ITU-R 5.138, ITU-R 5.150, ITU-R 5.280, and IMT-2000. It would be evident to one skilled in the art that many portable and fixed electronic devices may support multiple wireless protocols simultaneously, such that for example a user may employ GSM services such as telephony and SMS and Wi-Fi/WiMAX data transmission, VOIP and Internet access. Accordingly portable electronic devices within first user group 900A may form associations either through standards such as IEEE 802.15 and Bluetooth as well in an ad-hoc manner.

Also connected to the network 900 are concrete mapping environment 965, State Body 970, and Bridge Structure environment 975 as well as first and second servers 990A and 990B which together with others not shown for clarity, may host according to embodiments of the inventions multiple services associated with one or more organizations, including but not limited to, a provider of the software operating system(s) and/or software application(s) associated with the electronic device(s), a provider of the electronic device, provider of one or more aspects of wired and/or wireless communications, provider of the electrical measurement devices, provider of mapping analysis software, provider of electrical measurement analysis software, global position system software, materials databases, building databases, regulatory databases, license databases, construction organizations, websites, and software applications for download to or access by FEDs, PEDs, and electrical measurement systems. First and second servers 990A and 990B may also host for example other Internet services such as a search engine, financial services, third party applications and other Internet based services.

Accordingly, it would be evident to one skilled in the art that electrical measurement systems and/or concrete corrosion analysis according to embodiments of the invention described supra in respect of FIGS. 4 through 8 may be connected to a communications network such as network 900 either continuously or intermittently. It would be further evident that the electrical resistivity measurements of concrete and/or rebar together with the analysis of the measurements and their mapping may be triggered as a result of activities triggered by, for example, the Government Body 960A and/or State Body 970 in order to address regulatory requirements, safety concerns etc.

Accordingly, the engineers, workers and/or technicians who will be performing the measurements may be able to access Bridge Structure Environment 975 to obtain architect drawings, engineering data, design data, etc relating to the concrete structure being assessed. It would be evident that other databases addressing other environments such as for example, shopping malls, road surfaces, public walkways, residential housing, and commercial buildings may be accessed where the requirements for assessment relate to these structures and the regulatory bodies may be similarly transportation or include others such as Department of Housing, Federal Highway Department, and Bureau of Industry and Security. Where all or part of the structure being assessed has been previously assessed then data may be retrieved from the Concrete Mapping Environment for example. It would be evident that with coordinated based measurement acquisition that an engineer may view in real time a contour map of the structure being assessed as the data is acquired and accordingly may ask for additional measurements or repeated measurements to be performed.

Additionally, previous contour mapping and electrical measurements may allow for targeted re-assessment of areas of concern at a different frequency to that of the overall structure.

Figure 10:
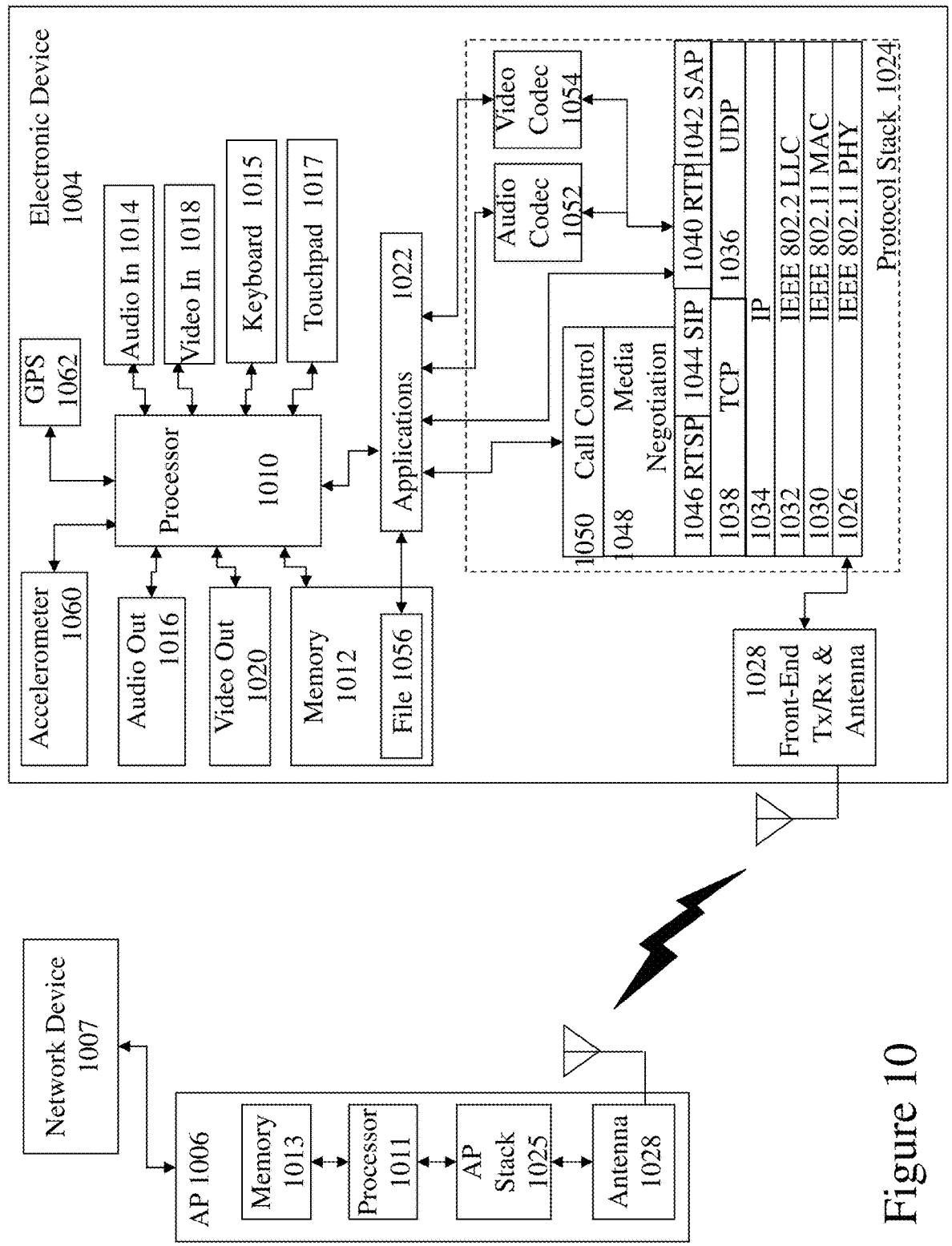
FIG. 10 depicts an electronic device and network access point supporting contextual based UIs according to embodiments of the invention.

FIG. 10 there is depicted an electronic device 1004 and network access point 1007 supporting contextual based UIs according to embodiments of the invention. Electronic device 1004 may for example be a portable electronic device or a fixed electronic device and may include additional elements above and beyond those described and depicted. Also depicted within the electronic device 1004 is the protocol architecture as part of a simplified functional diagram of a system 1000 that includes an electronic device 1004, such as a smartphone 955, an access point (AP) 1006, such as first AP 910, and one or more network devices 1007, such as communication servers, streaming media servers, and routers for example such as first and second servers 990A and 990B respectively. Network devices 1007 may be coupled to AP 1006 via any combination of networks, wired, wireless and/or optical communication links such as discussed above in respect of FIG. 9. The electronic device 1004 includes one or more processors 1010 and a memory 1012 coupled to processor(s) 1010. AP 1006 also includes one or more processors 1011 and a memory 1013 coupled to processor(s) 1011. A non-exhaustive list of examples for any of processors 1010 and 1011 includes a central processing unit (CPU), a digital signal processor (DSP), a reduced instruction set computer (RISC), a complex instruction set computer (CISC) and the like. Furthermore, any of processors 1010 and 1011 may be part of application specific integrated circuits (ASICs) or may be a part of application specific standard products (ASSPs). A non-exhaustive list of examples for memories 1012 and 1013 includes any combination of the following semiconductor devices such as registers, latches, ROM, EEPROM, flash memory devices, non-volatile random access memory devices (NVRAM), SDRAM, DRAM, double data rate (DDR) memory devices, SRAM, universal serial bus (USB) removable memory, and the like.

Electronic device 1004 may include an audio input element 1014, for example a microphone, and an audio output element 1016, for example, a speaker, coupled to any of processors 1010. Electronic device 1004 may include a video input element 1018, for example, a video camera, and a video output element 1020, for example an LCD display, coupled to any of processors 1010. Electronic device 1004 also includes a keyboard 1015 and touchpad 1017 which may for example be a physical keyboard and touchpad allowing the user to enter content or select functions within one of more applications 1022. Alternatively the keyboard 1015 and touchpad 1017 may be predetermined regions of a touch sensitive element forming part of the display within the electronic device 1004. The one or more applications 1022 that are typically stored in memory 1012 and are executable by any combination of processors 1010. Electronic device 1004 also includes accelerometer 1060 providing three-dimensional motion input to the process 1010 and GPS 1062 which provides geographical location information to processor 1010.

Electronic device 1004 includes a protocol stack 1024 and AP 1006 includes a communication stack 1025. Within system 1000 protocol stack 1024 is shown as IEEE 802.11 protocol stack but alternatively may exploit other protocol stacks such as an Internet Engineering Task Force (IETF) multimedia protocol stack for example. Likewise AP stack 1025 exploits a protocol stack but is not expanded for clarity. Elements of protocol stack 1024 and AP stack 1025 may be implemented in any combination of software, firmware and/or hardware. Protocol stack 1024 includes an IEEE 802.11-compatible PHY module 1026 that is coupled to one or more Front-End Tx/Rx & Antenna 1028, an IEEE 802.11-compatible MAC module 1030 coupled to an IEEE 802.2-compatible LLC module 1032. Protocol stack 1024 includes a network layer IP module 1034, a transport layer User Datagram Protocol (UDP) module 1036 and a transport layer Transmission Control Protocol (TCP) module 1038.

Protocol stack 1024 also includes a session layer Real Time Transport Protocol (RTP) module 1040, a Session Announcement Protocol (SAP) module 1042, a Session Initiation Protocol (SIP) module 1044 and a Real Time Streaming Protocol (RTSP) module 1046. Protocol stack 1024 includes a presentation layer media negotiation module 1048, a call control module 1050, one or more audio codecs 1052 and one or more video codecs 1054. Applications 1022 may be able to create maintain and/or terminate communication sessions with any of devices 1007 by way of AP 1006. Typically, applications 1022 may activate any of the SAP, SIP, RTSP, media negotiation and call control modules for that purpose. Typically, information may propagate from the SAP, SIP, RTSP, media negotiation and call control modules to PHY module 1026 through TCP module 1038, IP module 1034, LLC module 1032 and MAC module 1030.

It would be apparent to one skilled in the art that elements of the electronic device 1004 may also be implemented within the AP 1006 including but not limited to one or more elements of the protocol stack 1024, including for example an IEEE 802.11-compatible PHY module, an IEEE 802.11-compatible MAC module, and an IEEE 802.2-compatible LLC module 1032. The AP 1006 may additionally include a network layer IP module, a transport layer User Datagram Protocol (UDP) module and a transport layer Transmission Control Protocol (TCP) module as well as a session layer Real Time Transport Protocol (RTP) module, a Session Announcement Protocol (SAP) module, a Session Initiation Protocol (SIP) module and a Real Time Streaming Protocol (RTSP) module, media negotiation module, and a call control module.

Portable and fixed electronic devices represented by electronic device 1004 may include one or more additional wireless or wired interfaces in addition to the depicted IEEE 802.11 interface which may be selected from the group comprising IEEE 802.15, IEEE 802.16, IEEE 802.20, UMTS, GSM 850, GSM 900, GSM 1800, GSM 1900, GPRS, ITU-R 5.138, ITU-R 5.150, ITU-R 5.280, IMT-2000, DSL, Dial-Up, DOCSIS, Ethernet, G.hn, ISDN, MoCA, PON, and Power line communication (PLC).

Figure 4B:
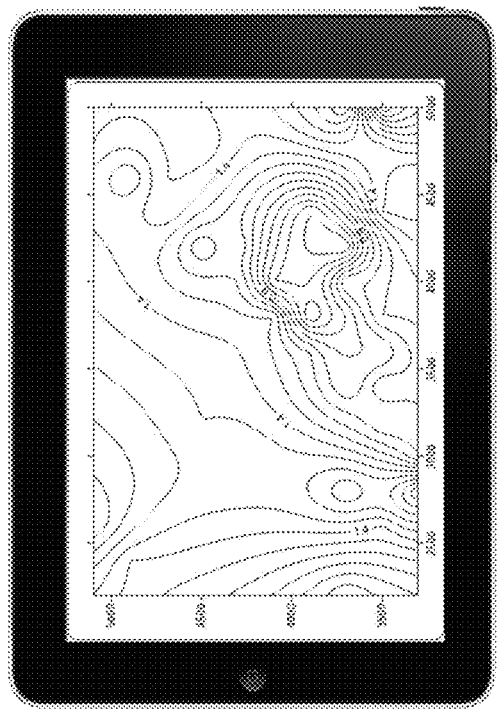
Figure 4B:
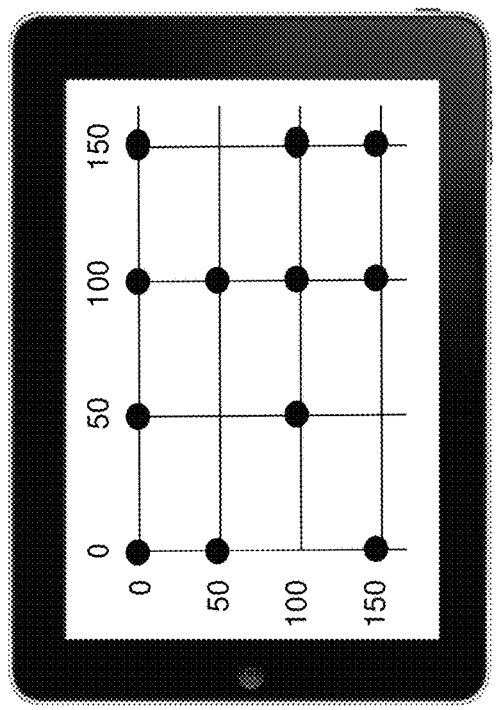

Accordingly, it would be evident to one skilled in the art that the electronic device 1004 may be, for example, the tablet PC 450 in FIG. 4 or the multimeter 410B and/or meter 480 in FIG. 4 wherein the wireless network access, GPS, etc form part of these electrical measurements systems rather than a separate PED. Alternatively, electronic device 1004 may be a PED wirelessly interconnected to the electrical measurement system allowing an on-site engineer for example to view the contour mapping and/or electrical data in real time as well as accessing the other information resources such as described above in respect of FIG. 9. Accordingly, an on-site engineer can decide on taking more measurements from a particular location, and make immediate suggestions about the safety of the reinforced concrete structure.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above and/or a combination thereof.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages and/or any combination thereof. When implemented in software, firmware, middleware, scripting language and/or microcode, the program code or code segments to perform the necessary tasks may be stored in a machine readable medium, such as a storage medium. A code segment or machine-executable instruction may represent a procedure, a function, a subprogram, a program, a routine, a subroutine, a module, a software package, a script, a class, or any combination of instructions, data structures and/or program statements. A code segment may be coupled to another code segment or a hardware circuit by passing and/or receiving information, data, arguments, parameters and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor and may vary in implementation where the memory is employed in storing software codes for subsequent execution to that when the memory is employed in executing the software codes. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels and/or various other mediums capable of storing, containing or carrying instruction(s) and/or data.

The methodologies described herein are, in one or more embodiments, performable by a machine which includes one or more processors that accept code segments containing instructions. For any of the methods described herein, when the instructions are executed by the machine, the machine performs the method. Any machine capable of executing a set of instructions (sequential or otherwise) that specify actions to be taken by that machine are included. Thus, a typical machine may be exemplified by a typical processing system that includes one or more processors. Each processor may include one or more of a CPU, a graphics-processing unit, and a programmable DSP unit. The processing system further may include a memory subsystem including main RAM and/or a static RAM, and/or ROM. A bus subsystem may be included for communicating between the components. If the processing system requires a display, such a display may be included, e.g., a liquid crystal display (LCD). If manual data entry is required, the processing system also includes an input device such as one or more of an alphanumeric input unit such as a keyboard, a pointing control device such as a mouse, and so forth.

The memory includes machine-readable code segments (e.g. software or software code) including instructions for performing, when executed by the processing system, one of more of the methods described herein. The software may reside entirely in the memory, or may also reside, completely or at least partially, within the RAM and/or within the processor during execution thereof by the computer system. Thus, the memory and the processor also constitute a system comprising machine-readable code.

In alternative embodiments, the machine operates as a standalone device or may be connected, e.g., networked to other machines, in a networked deployment, the machine may operate in the capacity of a server or a client machine in server-client network environment, or as a peer machine in a peer-to-peer or distributed network environment. The machine may be, for example, a computer, a server, a cluster of servers, a cluster of computers, a web appliance, a distributed computing environment, a cloud computing environment, or any machine capable of executing a set of instructions (sequential or otherwise) that specify actions to be taken by that machine. The term "machine" may also be taken to include any collection of machines that individually or jointly execute a set (or multiple sets) of instructions to perform any one or more of the methodologies discussed herein.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method comprising;
generating with an electrical measurement system an electrical signal of predetermined characteristics;
applying the electrical signal to a first predetermined portion of a concrete structure with a first electrical probe;
measuring with the electrical measurement system an output electrical signal with a second electrical probe applied to a second predetermined portion of the concrete structure, the output electrical signal being the result of application of the generated electrical signal to the first predetermined portion of the concrete structure;
applying predetermined signal processing to the output electrical signal to generate a processed output; and
determining a characteristic of the concrete structure in dependence upon an aspect of the processed output.

2. The method according to claim 1, wherein
the electrical signal is a voltage pulse;
the output electrical signal is a measured output voltage measured over a predetermined period of time;
the processed output comprises gain and phase versus frequency; and
the aspect of the processed output is the low frequency characteristics of the processed output.

3. The method according to claim 1, wherein
the electrical signal is either a narrow DC current pulse or a narrow DC voltage pulse;
the output electrical signal is a measured output voltage measured over a predetermined period of time;
the processed output comprises variations of gain and phase versus frequency; and
the aspect of the processed output is a low frequency impedance established in dependence upon a low frequency portion of the established variations of gain and phase versus frequency.

4. The method according to claim 3, wherein
either:
the applied signal is coupled directly to the rebar within the concrete structure;
or
the applied signal is induced within the rebar within the concrete structure through electromagnetic induction.

5. The method according to claim 3, wherein
the second electrical probe is one of a plurality of second electrical probes disposed across the concrete structure; and
the first electrical probe applies the electrical signals to a plurality of rebar elements electrically connected to each other within the concrete structure.

6. The method according to claim 1, wherein
a portion of the concrete structure where the measurements are being made is covered by another material;
the first electrical probe is electrically connected to a surface of the concrete structure through a hole within the another material covering the surface of the concrete structure;
the second electrical probe is electrically connected to a rebar within the concrete structure; and
the first electrical probe is inserted into the hole formed within the another material covering the concrete structure which is filled with a fluid which is electrically conductive.

7. The method according to claim 1, wherein
the first electrical probe comprises a first pair of electrical contacts having a first spacing;
the second electrical probe comprises a second pair of electrical contacts having a second spacing less than the first spacing;
the first pair of electrical contacts and the second pair of electrical contacts are aligned along a common line;
the applied electrical signal is a constant AC current established at a plurality of frequencies;
the output electrical signal is a voltage across the pair of second electrical contacts at a high sampling rate relative to each frequency of the plurality of frequencies;
the plurality of frequencies of the constant AC current are established between a first frequency and a second frequency;
the processed output comprises a voltage response of the output electrical signal with frequency; and
the characteristic of the concrete structure is a determination of whether a rebar within the concrete structure is corroded or not.

8. The method according to claim 7, wherein
a corroded re-bar exhibits a low frequency dependent variation of the output electrical signal with frequency; and
a non-corroded re-bar exhibits a high frequency dependent variation of the output electrical signal with frequency.

9. A system comprising;
an electrical measurement system comprising:
a first module generating an electrical signal of predetermined characteristics which is applied via a first electrical probe to a first predetermined portion of a concrete structure;
a measurement module generating an output electrical signal in dependence upon a measured electrical signal received from a second probe applied to a second predetermined portion of the concrete structure;
a signal processing module applying predetermined signal processing to the output electrical signal to generate a processed output; and
a determination module to establish a characteristic of the concrete structure in dependence upon an aspect of the processed output.

10. The system according to claim 9, wherein
the electrical signal is a voltage pulse;
the output electrical signal is a measured output voltage measured over a predetermined period of time;

the processed output comprises gain and phase versus frequency; and the aspect of the processed output is the low frequency characteristics of the processed output.

11. The system according to claim 9, wherein
the electrical signal is either a narrow DC current pulse or a narrow DC voltage pulse;
the output electrical signal is a measured output voltage measured over a predetermined period of time;
the processed output comprises variations of gain and phase versus frequency; and
the aspect of the processed output is a low frequency impedance established in dependence upon a low frequency portion of the established variations of gain and phase versus frequency.

12. The system according to claim 11, wherein either:
the applied signal is coupled directly to the rebar within the concrete structure;
or
the applied signal is induced within the rebar within the concrete structure through electromagnetic induction.

13. The system according to claim 11, wherein
the second electrical probe is one of a plurality of second electrical probes disposed across the concrete structure; and
the first electrical probe applies the electrical signals to a plurality of rebar elements electrically connected to each other within the concrete structure.

14. The system according to claim 9, wherein
a portion of the concrete structure where the measurements are being made is covered by another material;
the first electrical probe is electrically connected to a surface of the concrete structure through a hole within the another material covering the surface of the concrete structure;
the second electrical probe is electrically connected to a rebar within the concrete structure; and
the first electrical probe is inserted into the hole formed within the another material covering the concrete structure which is filled with a fluid which is electrically conductive.

15. The system according to claim 9, wherein
the first electrical probe comprises a first pair of electrical contacts having a first spacing;
the second electrical probe comprises a second pair of electrical contacts having a second spacing less than the first spacing;
the first pair of electrical contacts and the second pair of electrical contacts are aligned along a common line;
the applied electrical signal is a constant AC current established at a plurality of frequencies;
the output electrical signal is a voltage across the pair of second electrical contacts at a high sampling rate relative to each frequency of the plurality of frequencies;

the plurality of frequencies of the constant AC current are established between a first frequency and a second frequency;
the processed output comprises a voltage response of the output electrical signal with frequency; and
the characteristic of the concrete structure is a determination of whether a rebar within the concrete structure is corroded or not.

16. The system according to claim 15, wherein
a corroded re-bar exhibits a low frequency dependent variation of the output electrical signal with frequency; and
a non-corroded re-bar exhibits a high frequency dependent variation of the output electrical signal with frequency.

17. A method comprising;
providing a measurement system for determining a characteristic of the concrete structure in dependence upon a processed output generated in dependence upon one or more measured electrical signals measured with the measurement system;
providing a plurality of beacons, each beacon including a predetermined portion of a transceiver providing pulses of a predetermined format; and
providing a positioning system to provide a position;
determining a plurality of relative locations, each relative location being that of the measurement system relative to a predetermined subset of the plurality of beacons; and
storing at least one of the determined characteristic of the concrete structure, the processed output and the one or more measured electrical signals together with the plurality of relative locations and the position.

18. The method according to claim 17, wherein
the global positioning system forms part of at least one of a beacon of the plurality of beacons and the measurement system.

19. The method according to claim 17, wherein
the plurality of beacons employ a ranging technique to establish the plurality of relative locations; and
the ranging technique employs signals that are one of ultrasonic signals, acoustic signals, visible optical signals, infrared optical signals, visible laser based optical laser signals, infrared laser based optical signals, microwave signals, and radio frequency signals.

20. The method according to claim 17, wherein
the positioning system is one of a global positioning system.

21. The method according to claim 17, wherein
the positioning system is a local positioning system employing triangulation to one or more of cellular base stations, Wi-Fi access points, and radio broadcast towers.

* * * * *